Figure 1:
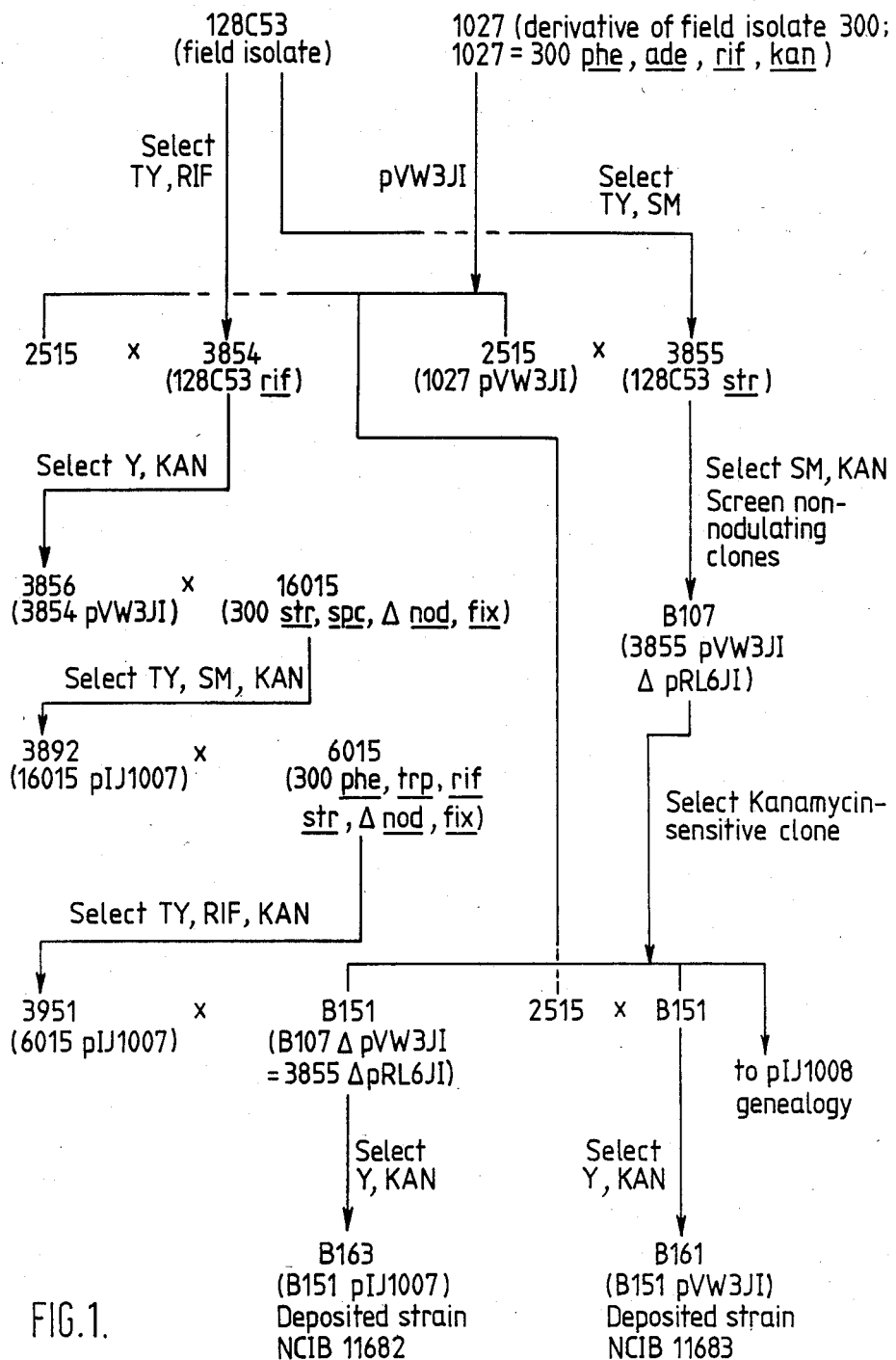

United States Patent [19]

Brewin et al.

[11] Patent Number: 4,567,146

[45] Date of Patent: Jan. 28, 1986

[54] SYNTHETIC PLASMID AND BACTERIA CONTAINING IT

[75] Inventors: Nicholas J. Brewin, Cringleford; Andrew W. B. Johnston, Little Melton, both of England

[73] Assignee: National Research Development Corporation, London

[21] Appl. No.: 318,417

[22] Filed: Nov. 5, 1981

[51] Int. Cl.[4] .................. C12N 15/00; C12N 1/20; C12N 1/00; C12P 13/00; C12R 1/41

[52] U.S. Cl. .............................. 435/172.3; 435/128; 435/253; 435/878; 435/317; 435/29; 435/56; 435/72

[58] Field of Search ............... 435/172, 317, 253, 878, 435/128, 168, 172.3; 71/6, 7, 8

[56] References Cited

PUBLICATIONS

Brewin et al.: Nature 288, 77 (1980).
Brewin et al.: J. Gen. Microbiol. 116, 261 (1980).
Lim et al.: Trends in Biochemical Sciences, Jun. 1980, pp. 167–170.
Johnston et al.; in *Plasmids of Medical, Environmental and Commercial Importance*, Timmis et al., (ed.), Elsevier/North Holland, 1979, pp. 317–325.
Buchanan-Wollaston et al.; Molec. Gen. Genet. 178, 185 (1980).
Evans et al.; In Report of the Public Meeting on Genetic Engineering for Nitrogen Fixation, National Academy of Sciences, U.S. Govt. Printing Office, 1977, pp. 61–76.

*Primary Examiner*—Thomas G. Wiseman
*Assistant Examiner*—James Martinell
*Attorney, Agent, or Firm*—Oblon, Fisher, Spivak, McClelland & Maier

[57] ABSTRACT

Bacteria of the genus Rhizobium nodulate legumes and are responsible for nitrogen fixation. The energetics of this process are improved if hydrogen uptake ability (Hup) is imparted to the bacteria to "recycle" some of the hydrogen lost during the nitrogen fixation. Such Hup is observed in a naturally occurring strain of *Rhizobium leguminosarum* but it was not known how to transfer it to other strains. The present invention provides recombinant plasmids pIJ1008 and pIJ1007 which enable it to be transferred. These plasmids are formed from a transmissible plasmid, synthesized to include a drug-resistance marker, and a plasmid of the naturally occurring strain. Cultures containing the plasmids have been deposited in a culture collection and can be used, after appropriate further crosses as described, to impart Hup to other strains of Rhizobium. In addition, cultures containing the starting transmissible plasmids (pVW5JI and pVW3JI) have been deposited and can be used to prepare strains of Rhizobium containing the same or similar recombinant plasmids. Plant growth analysis in laboratory tests demonstrate that rhizobial strains containing these recombinant nodulation plasmids which confer Hup+ ability are superior to the corresponding Rhizobium field isolates in terms of overall plant growth dependent on symbiotic nitrogen fixation.

14 Claims, 2 Drawing Figures

SYNTHETIC PLASMID AND BACTERIA CONTAINING IT

This invention is in the field of bacterial genetics and relates to a synthetic plasmid, which is a chemical substance composed of DNA, and bacteria of the genus Rhizobium containing the plasmid.

Many legumes, for example peas, beans, clover and alfalfa, have an ability to take nitrogen from the air and transform it into protein. This process is called "nitrogen fixation". It is brought about by certain unicellular bacteria which dwell in the roots of the plants. Rhizobium is a particularly important genus of such bacteria. The Rhizobium bacterium penetrates the root hairs of the legume through an "infection thread" and which forms a "nodule" in which nitrogen is converted into ammonium of value to the plant.

The action of Rhizobia in nitrogen fixation shows a considerable degree of species specificity. That is, different species of legume normally show the beneficial effects of nitrogen fixation, often referred to as "symbiosis", only when acted on by the appropriate species of Rhizobium. Thus, Rhizobium leguminosarum has a high specificity to peas, Rhizobium phaseoli to beans, Rhizobium trifolii to clover and Rhizobium meliloti to alfalfa. The present invention is concerned most with the R. leguminosarum species.

Attempts have been made to find strains of species of Rhizobium having improved symbiotic properties. It would then be possible by inoculating the soil around the plants to improve crop yields and reduce the use of fertilizer to supply nitrogen. One method has been to select field isolates of Rhizobia, i.e. isolates from the legume plants which grow best. Another approach has been to carry out mutagenesis of field isolates, in the hope of producing mutant strains of Rhizobia with improved symbiotic properties. The present invention embodies a new approach, that of altering the properties of the Rhizobium bacterium by gene transfer, so that symbiotically favourable genetic characteristics from different field isolates are combined in a single new hybrid strain.

All naturally occurring strains of Rhizobium have the ability to form nodules and to fix nitrogen. These characteristics are herein referred to as "Nod" and "Fix" respectively. Strains which posses these characteristics are designated Nod+ and Fix+ respectively, to distinguish them from others (random mutants or synthetic strains) which do not, Nod− and Fix− symbols being applied to characterise these other strains.

Another favourable symbiotic trait is the capacity of a few strains to take up hydrogen. This hydrogen uptake ("Hup") characteristic aids in forming ATP and thereby compensates partially for the ATP—dependent loss of hydrogen catalysed by a nitrogenase enzyme complex as a result of nitrogen fixation. Thus, Rhizobium strains having the hydrogen uptake characteristic (Hup+) partially recycle energy which would otherwise become dissipated and are considered to be more effective symbiotically than Hup− strains. An example is the field isolate of R. leguminosarum known as 128C53.

The present inventors have now found that the Hup+ determinant can be transferred artifically into strains which were previously Hup− and that the Hup+ determinant is carried on a plasmid. They have also synthesised a novel plasmid carrying the Hup+ determinant and novel strains of R. leguminosarum containing it. These strains have been found to confer superior growth on the host plant, exceeding that given by the comparable field isolate naturally occurring or "wild type" strains.

Plasmids are components of a somatic cell which are made up of double-stranded DNA and replicate independently of the chromosomes. Generally, the molecule is circular and the molecular weight of the order of megadaltons (1 Md = $10^6$ daltons). Some plasmids are transmissible, a characteristic which is denoted herein by "Tra". That is they can transfer from one cell to another by conjugation (mating of one strain with another). Others are non-transmissible. Some plasmids can undergo recombination, which involves exchanges of segments of DNA. These exchanges can take place with chromosomes, with other plasmids or with segments of DNA transduced by phages. It is known that the nodulation ability of Rhizobia arises from genetic determinants carried by a plasmid. The present inventors have found that hydrogen uptake ability is also produced by plasmid genes and that it is possible to co-transfer these characteristics together with nitrogen fixation ability from one cell to another by conjugation. To do this, a recombinant plasmid was synthesised from a plasmid which was transmissible but had no hydrogen uptake ability and a plasmid which had nodulation, nitrogen fixation and hydrogen uptake ability but which was not transmissible. The synthesis was carried out by two bacterial crosses in vivo.

In summary the invention provides such recombinant plasmids, bacteria of the genus Rhizobium containing them, a method of synthesising these or similar recombinant plasmids and bacteria containing them, a method of using the recombinant plasmids to construct further useful strains of Rhizobium and legumes infected with Rhizobium containing the novel recombinant plasmid. While the invention has particular reference to R. leguminosarum, it is potentially useful in relation to other species of Rhizobia.

The recombinant plasmids of the present invention are defined by reference to cultures of strains of Rhizobium leguminosarum deposited at the National Collection of Industrial Bacteria, Torry Research Station, P O Box 31, 135 Abbey Road, Aberdeen Scotland AB9 8DG on Oct. 22, 1981. They are as follows:

Strain B164
NCIB Accession number: 11684

| Characteristics: | Str, Kan, | Nod+, | Fix+, | Hup+, | Tra+ |
|---|---|---|---|---|---|
| Plasmids: | pRL13JI | m.w. | 250 Md | | |
| | pIJ1008 | m.w. | 195 Md | | | pIJ1008 is defined as the plasmid of lower molecular weight, which migrates fastest on agarose gel in the gel electrophoresis described hereinafter.

Strain B163
NCIB Accession number: 11682

| Characteristics: | Str, Kan, | Nod+, | Fix+, | Hup+, | Tra+ |
|---|---|---|---|---|---|
| Plasmids: | pRL13JI | m.w. | 250 Md | | |
| | pIJ1007 | m.w. | 195 Md | | | pIJ1007 is defined as the plasmid of lower molecular weight, which migrates fastest on agarose gel in the gel electrophoresis described hereinafter.

Plasmids can be isolated from these cultures in the manner described hereinafter.

The invention includes a culture of the bacteria of the genus Rhizobium containing plasmid pIJ1007 or pIJ1008. Such plasmids are of general utility in modifying the properties of the Rhizobium bacterium, and in particular for their beneficial effect on the hydrogen uptake ability of *R. leguminosarum*. The cultures can be produced in substantially pure form, i.e. so that they are substantially free at least of the donor and recipient strains from which they were formed. The strains cultured can, of course, contain one or more other compatible plasmids.

The invention includes a method of preparing a culture of bacteria of the genus Rhizobium containing a recombinant plasmid which method is characterised in that:

(1) in a first cross, a donor strain of Rhizobium containing (a) a plasmid lacking genes coding for nodulation, but which is transmissible, is crossed with a recipient strain of Rhizobium carrying (b) a plasmid having genes coding for nodulation, nitrogen fixation and hydrogen uptake ability, but which is non-transmissible, whereby a transconjugant strain carrying a plasmid which is formed from said plasmids (a) and (b), and is a conjugal precursor of a recombinant plasmid (c) formed from said plasmids (a) and (b), said recombinant plasmid (c) having genes coding for nodulation, nitrogen fixation and hydrogen uptake ability and being transmissible, is obtained;

(2) said transconjugant strain is separated from donor and recipient strains and cultured to produce a substantially pure culture thereof;

(3) in a second cross, the transconjugant strain from the first cross is used as a donor strain and crossed with a plasmid-containing recipient strain, whereby a transconjugant strain carrying a recombinant plasmid (c) is obtained; and (4) said transconjugant strain from the second cross is separated from donor and recipient strains and cultured to produce a substantially pure culture thereof.

In the above method the starting transmissible plasmid conveniently carries a selectable determinant preferably drug-resistance genes. These can be inserted into a known transmissible plasmid by use of a suitable DNA transposon. The Kanamycin resistance transposon Tn5, well known in itself, has been used successfully to prepare two starting transmissible plasmids herein designated pVW5JI and pVW3JI. Strains containing these plasmids have been deposited at the National Collection of Industrial Bacteria, supra, on Oct. 22, 1981, as follows:

Strain: B162
NCIB Accession number: 11685

| Characteristics: | Str, Kan, | Nod−, | Tra+ |
|---|---|---|---|
| Plasmids: | pRL13JI | m.w. | 250 Md |
| | pVW5JI | m.w. | 165 Md |

Strain: B161
NCIB Accession number: 11683

| Characteristics: | Str, Kan, | Nod−, | Tra+ |
|---|---|---|---|
| Plasmids: | pRL13JI | m.w. | 250 Md |
| | pVW3JI | m.w. | 130 Md |

In each case the plasmid of lower molecular weight, which migrates fastest on agarose gel in the gel electrophoresis described hereinafter, is the desired transmissible plasmid.

Each cross produces only a relatively few transconjugants, which have to be selected from the donor and recipient strains. The preferred strain having Kanamycin resistance imparted by pVW5JI or pVW3JI is preferably chosen so as to be auxotrophic, i.e. to require supplements to the minimal medium on which the wild type from which it is derived is grown. The recipient strain conveniently has resistance to another drug, for example rifampicin. It is then possible to select transconjugants from this cross by plating them onto a minimal medium containing Kanamycin. Donor strains will then be unable to grow because they cannot survive on minimal medium, while recipient strains will be killed because they lack Kanamycin resistance. In this way it is possible to select transconjugants to which Kanamycin resistance genes have been transferred from the donor strain to the recipient. When the resultant transconjugant strain is used in a second cross as the donor strain, it is preferred to use a recipient strain with a different drug resistance characteristic, e.g. resistance to streptomycin. It is then possible to select transconjugants from the second cross by plating them onto a medium containing Kanamycin and streptomycin. The donor strain lacks streptomycin resistance while the recipient lacks Kanamycin resistance, so both will be killed. Kanamycin-resistant transconjugants can then readily be selected. By suitable exercise of choice of strains, it is therefore possible to devise many different ways of selecting for Kanamycin resistance transfer.

In the method of preparation described above, the first cross produces a Kan product which is Nod+, Fix+, but in which the plasmid cannot be detected by gel electrophoresis. This is possibly a cointegrate plasmid, but clearly it is some kind of precursor which yields a recombinant plasmid when the second cross is performed. (The scientific evidence is given more fully in Example 1).

Since the method described above is repeatable, it is expected that variant plasmids having similar properties to pIJ1008 and pIJ1007 will result. Accordingly, the present invention includes a recombinant plasmid characterised in that it contains DNA of:

(1) a first plasmid identifiable as being the same as the plasmid pVW5JI or pVW3JI of lower molecular weight present in the culture of a strain of *Rhizobium leguminosarum* NCIB 11685 or 11683 respectively;

(2) a second plasmid found in bacteria of another strain of *Rhizobium leguminosarum*, said second plasmid having genes coding for nodulation, nitrogen fixation and hydrogen uptake ability but which is non-transmissible. When the second plasmid is that of m.w. 190 Md found in *R. leguminosarum* 128C53, pIJ1008 or pIJ1007 will be obtained. Other plasmids having the defined characteristics for the second plasmid will give somewhat different recombinants, but these are within the concept of the invention as pertaining to a procedure for making the hydrogen uptake gene transmissible.

It will be apparent that plasmids pIJ1008 and pIJ1007 can be introduced into many strains of *Rhizobium leguminosarum* starting from the deposited cultures containing these plasmids; one general method is characterised in that:

(1) a strain of *Rhizobium leguminosarum* NCIB 11684 or 11682, as a donor strain, is crossed with a recipient strain of *Rhizobium leguminosarum* to produce a Kanamycin-resistant transconjugant strain, said recipient strain being one which permits selection of the transconjugant strain against the donor and recipient strains and which allows the transconjugant strain to be selected against when used as a donor in a subsequent cross with another strain of *Rhizobium leguminosarum*;

(2) said transconjugant strain is separated from the donor and recipient strains and cultured to produce a substantially pure culture thereof;

(3) in a second cross the transconjugant strain obtained from the first cross is used as a donor strain and crossed with a recipient strain of *Rhizobium leguminosarum* to produce a Kanamycin-resistant transconjugant strain and;

(4) said transconjugant strain from the second cross is separated from the donor and recipient strains to produce a substantially pure culture thereof.

Again it is convenient to choose an auxotrophic recipient strain for the first cross which also has at least one drug resistance marker other than Kanamycin. The recipient strain for the second cross can be a naturally occurring strain, e.g. from a field isolate such as 3622 or 300 which are per se known. A more detailed procedure is illustrated in Example 4.

Similarly the starting transmissible plasmids pVW3JI and pVW5JI can be transferred to many different host strains, starting from the deposited cultures thereof. Conveniently the culture strain is crossed with an auxotrophic strain, so that when these derivatives are crossed with a new host strain the transconjugants can then be selected on minimal medium containing Kanamycin.

Figure 2:
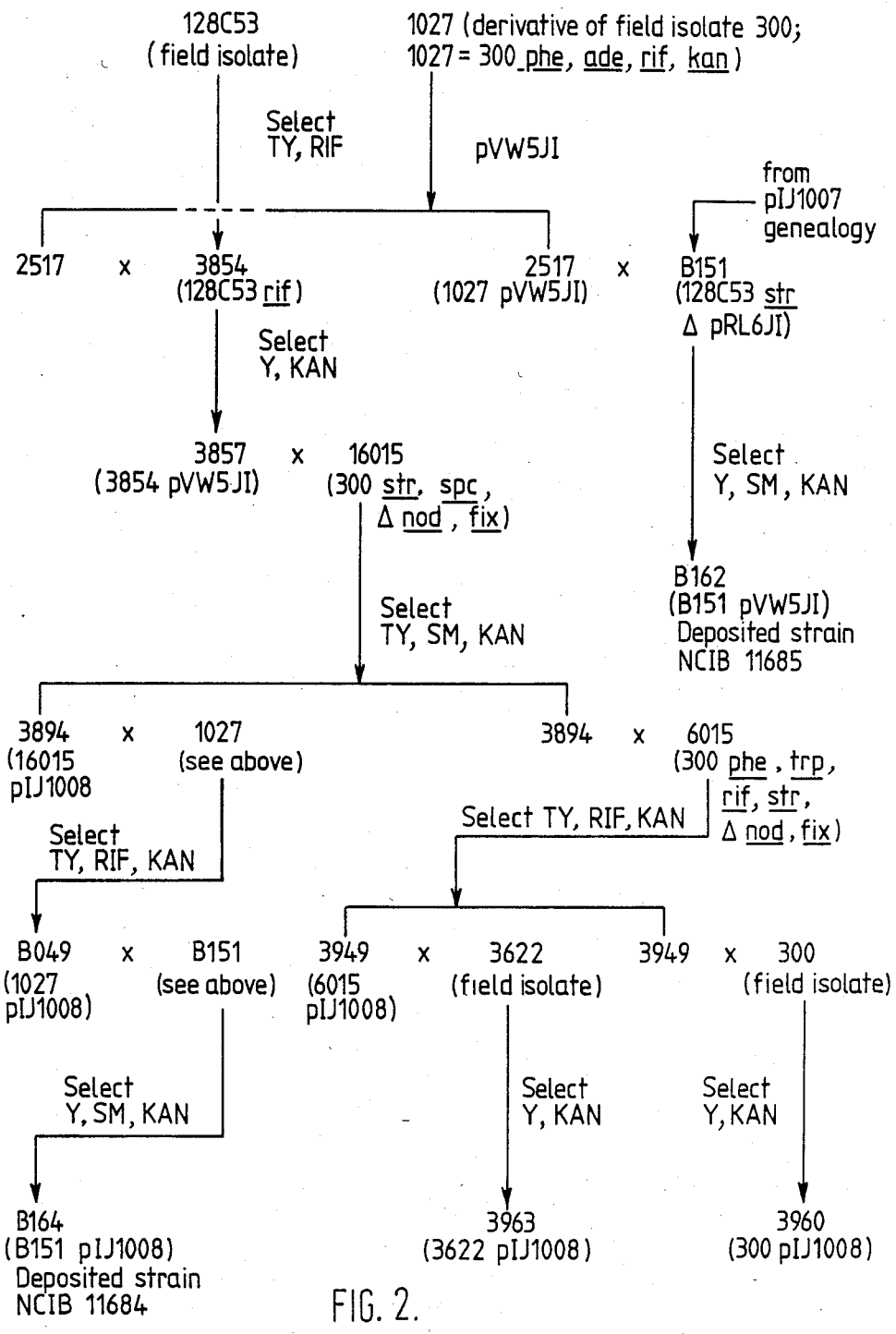

FIGS. 1 and 2 are two genealogical charts showing the origins of the strains of *Rhizobium leguminosarum* referred to in this application, including the deposited strains. An appendix at the end of the specification contains a key to notation and symbols used.

In the illustrative Examples which follow the following procedures were employed:

PROCEDURE FOR GENETIC CROSS

The procedure used is that of Beringer et al., Journal of General Microbiology, 104, 201-207 (1978).

1. Grow cultures of donor and recipient strains on separate agar slants containing TY medium (see below) at 28° C.
2. Resuspend in 3 ml. sterile water (c.$10^9$ bacteria/ml.)
3. Mix 0.5 ml of donor cultures with 0.5 ml. of recipient cultures. Transfer the mixture to a 45 mm. "Millipore" membrane on a petri dish containing TY agar.
4. Allow the liquid to dry off in a sterile laminar flow air hood for 2 hours.
5. Incubate the petri dish for 16 hours at 28° C.
6. Wash the bacteria off the membrane into 5 ml. of sterile water.
7. Make serial 10-fold dilutions and plate (0.1 ml.) bacteria on agar plates which permit growth of donor, recipient or transconjugant colonies only.
8. Repurify transconjugant clones by re-streaking to single colonies 2-3 times on selective media, for example on a minimal medium containing 40 micrograms/ml. of Kanamycin sulphate to select kanamycin-resistant colonies.

The media employed were:

| | |
|---|---|
| Difco Bactotryptone | 5 g. |
| Difco Bacto-yeast extract | 3 g. |
| CaCl$_2$.6H$_2$O | 1.3 g. |
| Agar | 15 g. |
| Distilled water to make | 1 liter. |

MINIMAL Y MEDIUM ("Y")

This is the "SY" medium of Beringer, Journal of General Microbiology 84, 188-198 (1974). See also Sherwood, Journal of Applied Bacteriology 33, 708-713 (1970). The antibiotics used were:

| | | |
|---|---|---|
| Kanamycin sulphate | 40 micrograms/ml. | "KAN" |
| Rifampicin | 20 micrograms/ml. | "RIF" |
| Streptomycin sulphate | 200 micrograms/ml. | "SM" |

ISOLATION OF PLASMIDS

Sterile solutions and glassware were used throughout. Centrifuge tubes and plastic beakers were washed with 75% ethanol if not autoclaved.

The following recipe and materials were used to lyse the cells and make plasmid preparations from all the strains described in this specification. Chromosomal DNA is removed by precipitation with detergent and sodium chloride. The supernatant contains plasmid DNA which is precipitated by polyethylene glycol.

STOCK SOLUTIONS USED

| TE buffer: pH 8.0 | 10 × TE stock (pH 8.0) |
|---|---|
| Tris: 50 mM | Tris base = 60.57 g/l |
| EDTA: 20 mM | EDTA = 74.45 g/l |

PA medium:
peptone: 0.4%
MgSO$_4$: per liter, 2 ml of 1 M MgSO$_4$ (0.5 g MgSO$_4$.7H$_2$O/1)
Tris borate electrophoresis buffer:
10 × concentrated stock solution:
per liter: 108 g Tris
9.3 g EDTA        } pH 8.3
55 g boric acid
Enzyme - protease type VI or XIV (Sigma)

RECIPE

1. Grow in 200 ml PA medium cultures of the R. leguminosarum for (c.$10^9$ bacteria) at 28° C. until mid-late log phase (not very turbid) (overnight). The PA medium is more suitable than TY for the purpose of isolating the plasmids.
2. Harvest by centrifuging at 10 krpm for 10-15 min, wash with 20 ml TE buffer and respin at 10 krpm. (Cell wet weight should be 0.4-0.6 g.)
3. Resuspend in 16 ml TE and transfer to a sterile 250 ml flask.
4. Add 2 ml protease (5 mg/ml in TE, predigested 1 h, 37° C.) and 2 ml SDS (sodium dodecyl sulphate, as a 10% W/V suspension in TE buffer). Gently roll the flask to mix. Cover and leave standing on ice for 45-60 min.
5. Transfer from ice to room temperature and leave until the lysate is clear (about 1 h). The lysate should be very viscous.
6. Titrate to pH 12.4 using 3M NaOH, (0.5 ml/20 ml lysate). Gently roll the flask to mix and leave 20 min at room temperature.

7. Titrate to pH 8.5 using 2M Tris-HCl pH 7.0 (1.5 ml). Swirl flask very gently until the Tris is evenly mixed in.
8. Add 5M NaCl (cold) to give 1M NaCl (i.e. need about 5.5 ml for 20 ml lysate and 2 ml added during titration) and decant into a plastic tube for SS34 Sorvall rotor (40 ml capacity). Mix by slow inversion of tube. Store on ice for 4 hr or overnight.
9. Clear lysate by sedimentation of SDS/NaCl; spin at about 15 krpm for 20 min in Sorvall SS34 at 4° C. (without the brake). Decant supernatant to fresh centrifuge tube and spin again if any flecks of SDS/NaCl precipitate remain. Decant the supernatant into a clear (polycarbonate) Sorvall tube containing 6.5 ml 50% PEG (polyethylene glycol m.w. 6000), to give 10% PEG final concentration.
10. Mix by inversion of tube or slow rolling horizontally on the bench. Store on ice overnight.
11. Sediment PEG/DNA by spinning at about 10 kprm for about 15 min, 4° C. Discard supernatant, drain tubes well before adding 0.3–0.5 ml TE containing 0.1% DEP (1 μl/ml, TE) to pellet. Leave on ice or in cool place to redissolve; (accelerate by gentle "rolling" of the tube if necessary).
12. Transfer DNA in TE to Eppendorf tube (pouring slowly). Store at 4° C.

The resultant "crude plasmid preparation" is suitable for analysis by gel electrophoresis.

For large scale plasmid preparations, the volumes were increased 10-fold and 4.5 ml of the DNA solution was added to a solution of 30 g CsCl dissolved in 25 ml TE, followed by 2.6 ml ethidium bromide (10 micrograms/ml.) Plasmids were isolated from the agarose gels, by repeatedly extracting the ethidium bromide stain using cold isopropanol saturated with CsCl/TE solution and dialysis at 4° C. to remove CsCl.

Such a procedure, when applied to NCIB strains 11684, 11682, 11685 or 11683 should provide a preparation of plasmid DNA substantially enriched for pIJ1008, pIJ1007, pVW5JI, or pVW3JI respectively. The principle contaminant would be the larger plasmid (250 Md) common to all four of these strains and present in the original recipient B151. (However, because of its large size and consequent instability during caesium chloride purification proportionately very little of this large plasmid would be present in the mixture.) Plasmid DNA corresponding to pIJ1008 (for example) can be distinguished from other DNA by a technique involving differential DNA hybridisation as described below.

The plasmid pIJ1008 may be defined operationally as that DNA present in NCIB strain 11684 that is absent from strain B151. Such DNA may be identified in the following manner, using as starting material either plasmid preparations recovered from caesium chloride gradients, or cloned DNA fragments derived from strain 11684 by recombinant DNA technology or indeed using total DNA recovered from this strain. The DNA in question would be fragmented by digestion with a restriction enzyme and the fragments separated by gel electrophoresis. The fragments would then be immobilised by transfer to nitrocellulose membranes, denatured and renatured in the presence of $^{32}$P-radioactive DNA obtained either from B151 or from a strain containing pIJ1008, e.g. NCIB strain 11684. After hybridisation and washing to remove unbound radioactive DNA probe, the nitrocellulose membranes are transferred to an x-ray plate in order to detect by autoradiography those DNA fragments that had DNA sequence homology to the radioactive probe DNA. Fragments of DNA derived from pIJ1008 could then be recognised in that they would not hybridise to a radioactive probe containing B151 DNA but would hybridize to a probe of NCIB strain 11684.

By a similar technique, DNA from pIJ1007, pVW5JI and pVW3JI could be identified using NCIB strains 11682, 11685 or 11683, respectively. Strain B151 is obtainable from the Rhizobium collection at the John Innes Institute, Norwich, U.K. Alternatively, a similar strain could be derived from any of the four NCIB cultures 11682, 11683, 11684, 11685 by screening for spontaneous loss of the kanamycin-resistant plasmid. Such derivatives would be identified as kanamycin sensitive clones (still resistant to streptomycin) but when examined by agarose gel electrophoresis lysates should be found to lack the kanamycin resistant plasmid or any derivative thereof.

Gel Electrophoresis of Plasmids

The strains were analysed for plasmids by the well known gel electrophoresis method, using agarose gels and the technique of Hirsch et. al., infra. A horizontal Perspex apparatus giving a gel slab 13.3 cm wide, 14 cm long and 0.6 cm thick was used. Sample wells were formed 8 at a time using a Perspec comb with 8 teeth. Samples of crude plasmid preparations were centrifuged for 2 min in an Eppendorf 5412 centrifuge and 40 microliters of the supernatant were added to 15–20 microliters of loading dye (20% Ficoll 400,000,0.125% bromophenol blue, 50 mM EDTA) and loaded on the gel. Electrophoresis was performed on 0.7% Agarose (Seakem) in Tris-borate buffer (see above), at 25 mA and 100 V and 4° C. for 16–20 hours in the dark, with the gel slab covered with "Clingfilm" to prevent evaporation. The gel slab was then removed from the apparatus and stained for 20 min at 15° C. in Tris-borate buffer containing 0.5 microgram/ml ethidium bromide, removed and stood in water at 15° C. for 45–60 minutes, to de-stain the background. The gel was illuminated under UV light (366 nm) to visualise the plasmid bands, and was photographed.

The molecular weight estimations were made using known plasmids RP4 (36 Md), PTiC58 (130 Md) and C58 cryptic plasmid (260 Md), to provide reference bands. All molecular weights reported herein are approximate.

EXAMPLE 1

Preparation of strains containing plasmid pIJ1008

This Example can be understood more quickly by referring to the chart of the genealogy of plasmid pIJ1008 which is included as an Appendix to the Examples.

(a) The starting strains

The starting strains of R. leguminosarum were:
(i) The donor strain 2517. This is obtained by introducing the plasmid pVW5JI into a strain 1027, a derivative of the field isolate strain 300 and described by Hirsch et al., Journal of General Microbiology, 120, 403–412, (1980). 2517 has the genotypic characterisation 300 phe-1, ade-27, rif-45. Readers unfamiliar with these symbols should refer to the key to notation. (The numbers "1", "27", "45" merely designate different mutations and have no fundamental significance). pVW5JI is a transmissible plasmid of molecular weight 165 Md and is a Kanamycin-resistant derivative of the transmissible plasmid pRL4JI present in field isolate strain 309. The Kanamycin-resistance genes were introduced by inserting the known transposon Tn5 into this plasmid. Besides pVW5JI this strain contains 6 other plasmids, of m.w. 310, 285, 220, 165 (one other) and 100 (two).

pVW5JI is the plasmid of lower molecular weight present in strain B162 which has been deposited at the National Collection of Industrial Bacteria, previously mentioned, on 22nd Oct. 1981, under Accession Number 11685. Strain B162 contains two plasmids, pRL13JI, present in field isolate strain 128C53, of m.w. 250 Md and pVW5JI of molecular weight 165 Md.

(ii) The recipient strain 3854. This is a rifampicin-resistant spontaneous mutant of the field isolate strain 128C53. 3854 has the genotypic characterisation 128C53 rif-397, i.e. it has rifampicin resistance but no Kanamycin resistance. It contains plasmids pRL13JI of molecular weight 250 Md and pRL6JI of molecular weight 190 Md. These are the two plasmids present in the natural (non-mutant) field isolate strains 128C53. Strains similar to 3854 can be obtained by selecting rifampicin-resistant bacteria from cultures of the field isolate (by culturing on rifampicin, which will kill the non-rifampicin-resistant bacteria). Other drug resistance markers could be used instead of rifampicin, the only requirement being that the bacterium should not show Kanamycin resistance.

The strains designated 128C53 referred to herein are those in use and available from The John Innes Institute, Norwich, England. Other strains designated 128C53 are in use elsewhere in the world. Some workers have a strain 128C53 containing an additional, plasmid but this is not considered likely to affect the results of the present invention. Any strain 128C53 bearing an appropriate drug-resistance marker is likely to give similar results to that used in this Example.

(b) The first cross (2517×3854)

When strain 2517 (donor) was crossed with 3854 (recipient) as described above, Kanamycin-resistant colonies were selected and purified on Kanamycin. Kanamycin resistance is herein designated Kan or Kan-r. The resultant strain was designated 3857.

(c) Analysis of strain 3857

The only plasmid visible in strain 3857 was pRL13JI, (m.w. 250 Md) the larger of the two plasmids present in the recipient strain 3854. There was no sign of the smaller of these two plasmids, pRL6JI, or of the plasmid pVW5JI which had been introduced from the donor strain 2517.

(d) Starting strains for the second cross

The second cross is of strain 3857 (donor with a strain 16015 (recipient). This strain 16015 is a derivative of the natural field isolate strain 300. It has the genotypic characterisation str-37 and spc-54 and contains a plasmid designated pIJ1000. pIJ1000 (m.w=195 Md) corresponds to the plasmid pRL10JI (m.w=220 Md) found in strain 300 except for a 25 Md deletion which has eliminated genes for nodulation and also for nitrogen fixation. Besides pIJ1000 it contains 5 other plasmids.

(e) The second cross (3857×16015)

When strain 3857 was crossed with 16015 and Kanamycin-resistant colonies selected, the frequency of transfer of Kan genes was $5 \times 10^{-7}$ per recipient. The product strain was designated 3894.

(f) Plasmid analysis and properties of the product of the second cross

Gel electrophoresis, as described above, showed that strain 3894 carried the same plasmid bands as the recipient strain 16015.

The activity of strain 3894 (and others) was tested on pea root nodules as follows. "Alaska" peas (*Pisum sativum* L.) were grown in modified Leonard jar assemblies. The plants were inoculated with strains of *Rhizobium leguminosarum* and fed on a nitrogen-free nutrient solution. The plants were assayed 25 days after inoculation. Nodulation ability (Nod) was determined by examining the roots. Nitrogen fixation (Fix) was determined by measuring the amount of ethylene produced by the roots after being subjected to acetylene gas (quasi-reduction of acetylene). The method employed was that of Beyon et al, Journal of General Microbiology, 120, 421–429, (1980). Hydrogen uptake ability (Hup) was determined by incubating the roots for 30 minutes in 25 ml. vessels containing tritiated hydrogen gas (2.4% v/v; specific activity 2.4mCi m.mol$^{-1}$) in the presence of acetylene (10% v/v) to inhibit hydrogen production by nitrogenase. This method is described by Bethlenfalvay et al., Plant Physiology, 63, 816–820 (1979).

It was found that strain 3894 had acquired hydrogen uptake ability in addition to nodulation and nitrogen fixation ability, i.e. was Hup+, Nod+, Fix+. This was a surprising finding. These determinants are present in the recipient strain of the first cross, which is a strain of the 128C53 type, but the plasmids of that strain are non-transmissible. pVW5JI is a transmissible plasmid but separate experiments have showed it not to possess Nod or Hup. Therefore strain 3894 apparently possesses a recombinant plasmid formed from pVW5JI and pRL6JI. No such plasmid appeared on the map of plasmid bands obtained by gel electrophoresis. However, the existence of the recombinant plasmid was shown in other ways, as follows. Firstly, strain 3894 was crossed with a strain 6015, a derivative of strain 300 having the same plasmids as 16015 and therefore the same deletion of determinants for nodulation and nitrogen fixation. (Strain 6015 is 300 phe-1, trp-12, rif-392, str-37). Again, a selection was made of Kanamycin-resistant cells. It was found that the frequency of transfer of Kanamycin resistance had increased from $5 \times 10^{-7}$ in the previous cross (3857×16015) to $10^{-3}$ per recipient. The resultant transconjugant strain was found to be Nod+, Fix+, Hup+, these characteristcs being co-transferred with Kan-r with a frequency greater than 90%.

A second piece of evidence for the existence of a recombinant plasmid is that a plasmid of molecular weight 195 Md present in strain 3894 (3857×16015) hybridised to a probe of transposon Tn5.

Thirdly the existence of the plasmid of molecular weight 195 Md was confirmed by crossing strain 3894 with a non-nodulating strain B151, and selecting for Kan-r. The Kan-r transconjugants arose at a frequency of $10^{-3}$ per recipient. 5 clones per cross were tested and found to be Nod+, Fix+, Hup+. In all cases, the cells were lysed and subjected to plasmid analysis as previously described and found to contain a plasmid of molecular weight 195 Md which hybridised to Tn5 probe.

Fourthly, when the starting donor strain 2517 was crossed with recipient strain 16015, Kan-r was transferred at high frequency $5 \times 10^{-2}$ per recipient, but none of the 10 Kan-r transconjugant clones tested had nodulating ability. This indicates that the Nod+, Fix+, determinants found in the donor strain cannot have been transferred to the Kan-r strains isolated in the successive crosses carried out.

The plasmid of molecular weight 195 Md which hybridised to the Tn5 probe and which is present in strain 3894 and the product of the subsequent cross with strain 6015 is the plasmid pIJ1008. It is believed that the initial cross 2517×3854 led to a co-integrate plasmid of very large molecular weight, too large to be stable enough to identify by gel electrophoresis. Upon further crossing of the product strain 3857 with 16015 the co-integrate broke down into the more stable plasmid pIJ1008. This plasmid has the same molecular weight as a plasmid already present in strain 16015 and which remained after the cross. It was therefore hidden on the gel plate.

EXAMPLE 2

In this Example plant growth analysis way carried out to compare the symbiotic performance of *Rhizobium leguminosarum* containing plasmid pIJ1008 with the nearest comparable strains lacking pIJ1008 and deficient in hydrogen uptake ability.

Table 1 shows the strains assembled and prepared, together with their characteristic plasmids. The precise geneological derivation of strains 3960, 3963 and 3894, which are according to the present invention, is shown in a genealogical chart included as an appendix to these Examples.

Controls used

Except in the special case of strain 3740 (see below), the introduction of plasmids pVW5JI and pIJ1008 does not eliminate any of the resident plasmids from the recipient strains. Therefore the derivatives of strains 300 and 3622 containing pIJ1008 carried two copies of certain nod and fix genes. Therefore, a plasmid series was included in the study as an appropriate control for pIJ1008. pIJ1019 is a recombinant between pVW5JI and the non-transmissible nodulation plasmid pRL10JI of strain 300. It also contains two copies of nod and fix genes, but unlike pIJ1008, it does not carry the hup determinant. Thus, the plasmids formed by combining pVW5JI with pRL6JI or pRL10JI, termed pIJ1008 and pIJ1019, respectively (Table 2), were transferred into strains 300, 3622, and 16015 (Table 1). The appropriate control strains 3996 (300 pVW5JI) and B118 (3622 pVW5JI) nodulated peas effectively, but strain 16015 pVW5JI is Nod− and Fix−. Thus it was necessary to construct strain 3740, a Nod+, Fix+ derivative of 16015 pVW5JI in which the mutant plasmid pIJ1000 was replaced by pRL10JI, the natural nodulation plasmid of strain 300.

Plant culture

'Alaska' peas (*Pisum sativum* L.) were grown in a controlled environment chamber under a 14/10 hr light/dark cycle, 50% humidity, and photon flux density (400–700 nm) of 650 $\mu E.m^{-2}.s^{-1}$. The chamber temperature regime was 20°/15° C. during the strain comparisons without combined nitrogen and 21°/20° C. during the ontogenetic experiments with strains 3740 and 3894. The plants were grown in modified "Leonard jar" assemblies with a nitrogen-free nutrient solution. The nutrient solution was adjusted to pH 7.0 and changed less than 0.5 pH units during the course of the experiments. The complete Leonard jar assemblies were autoclaved before planting. Pea seeds weighing 0.21–0.23 g and containing 7.72±0.14 mg N were surface-sterilized with 95% ethanol, rinsed, and germinated on sterile paper towels with distilled water. Three days after seed imbibition the seedlings were selected for uniformity, planted in Leonard jar assemblies, and inoculated with specific *Rhizobium leguminosarum* strains (Table 1). *Measurements of symbiotic associations.* In the strain comparisons 13 sets of seven plants were inoculated with one of each of the 13 R. leguminosarum strains listed in Table 1 and were grown with N-free nutrient solution. After 35 days of growth the plants were harvested. Leaf area was determined with an area meter. Leaf dry weight and leaf N content were determined separately from the rest of the plant.

In the ontogenetic experiments plants were inoculated with strain 3740 (Hup−) or strain 3894 (Hup+) and grown in the presence of N-free nutrient solution. Seven plants from each treatment were harvested at six day intervals starting 11 days after imbibition and ending 44 days after. At each harvest, $C_2H_2$-dependent $C_2H_4$ production, referred to less rigorously as $C_2H_2$ reduction, and $H_2$ evolution were measured on excised root systems as described by Bethlenfalvay & Phillips, Plant Physiology, 60, 419–421 (1977). Incubation times were 15 min for $H_2$ evolution and 5 min for $C_2H_2$ reduction. Plant dry weights were determined after 48 hr at 75° C., and N content was measured by Kjeldahl analysis with techniques that did not detect $NO_3^-$ or $NO_2^-$. These techniques are described by Burris & Wilson in Methods in Enzymology, Vol. IV, 355–356 (1957). (Table 4).

Strain reisolation

At the conclusion of all experiments rhizobia were reisolated from root nodules and were identified on the basis of drug-resistance patterns. It was thereby confirmed that the root nodules had been formed by the appropriate strains of Rhizobia. Because derivatives containing pVW5JI and pIj1008 had identical drug resistance markers, it was also necessary in some cases to run electrophoretic gels of plasmids to distinguish these derivatives. Two nodules from each of four plants in each treatment were used for reisolation of Rhizobium. After surface sterilisation for 15–30 sec in sodium hypochlorite (10% w/v), the nodules were crushed, and streaked for single colonies on plates containing complete medium (tryptone and yeast extract; see Beringer, Journal of General Microbiology, 84, 188–198, (1974). Five clones per nodule were checked for drug resistance markers, and two clones per nodule for electrophoretic profiles of plasmids.

TABLE 1

| Characteristics of Rhizobium leguminosarum strains studied | | |
|---|---|---|
| Strain | Characters | Symbiotic Phenotype |
| 128C53 | field isolate | Nod+Fix+Hup+ |
| 300 | field isolate | Nod+Fix+Hup− |
| 3996 | 300 pVW5JI | Nod+Fix+Hup− |
| B121 | 300 pIJ1019 | Nod+Fix+Hup− |
| 3960 | 300 pIJ1008 | Nod+Fix+Hup+ |
| 3622 | field isolate TOM | Nod+Fix+Hup− |
| B118 | 3622 pVW5JI | Nod+Fix+Hup− |
| B119 | 3622 pIJ1019 | Nod+Fix+Hup− |
| 3963 | 3622 pIJ1008 | Nod+Fix+Hup+ |
| 16015 | 300 str-37, spc-54, Δ(nod fix)6007 | Nod− |
| 3740 | 16015 pVW5JI, pRL10JI | Nod+Fix+Hup− |

TABLE 1-continued

Characteristics of Rhizobium leguminosarum strains studied

| Strain | Characters | Symbiotic Phenotype |
|---|---|---|
| 3758 | 16015 pIJ1019 | Nod+Fix+Hup− |
| 3894 | 16015 pIJ1008 | Nod+Fix+Hup+ |

*Introduction of pRL10JI eliminated from strain 16015 the corresponding plasmid pIJ1000.

TABLE 2

Characteristics of Rhizobium leguminosarum plasmids studied

| Plasmid | Description | Markers | Approximate Molecular Wt. (Md) |
|---|---|---|---|
| pVW5JI | pR4JI::Tn5 | Kan-r, Tra+ | 165 |
| pRL4JI | Transmissible bacteriocinogenic plasmid (Note below) | Med+, Tra+ | 160 |
| pRL6JI | Nodulation plasmid of strain 128C53 | Nod+, Fix+, Hup+ | 190 |
| pRL10JI | Nodulation plasmid of strain 300 | Nod+, Fix+ | 220 |
| pIJ1000 | pRL10JI Δ(nod, fix) | — | 195 |
| pIJ1008 | pVW5JI/pRL6JI recombinant | Kan-r, Tra+, Nod+, Fix+, Hup+ | |
| pIJ1019 | pVW5JI/pRL10JI recombinant | Kan-r, Tra+, Nod+, Fix+ | 155 |

Note:
pRL4JI is the Med+ Nod− plasmid present in field isolate strain 309. It is described by Hirsch et al., Journal of General Microbiology, 120, 403–412, (1980), and available from the John Innes Institute, Dept. of Genetics, Colney Lane, Norwich NR4 7UH, England.

TABLE 3

Effects of Rhizobium leguminosarum strains on plant growth and N assimilation

Peas were grown for 35 days in the absence of combined N before harvest. Strain 16015 formed no root nodules.

| Rhizobium strain | Dry weight (g/plant) | N content (mg/plant) | Leaf area (cm²/plant) | N concentration (%) |
|---|---|---|---|---|
| 128C53 | 4.05 | 138 | 333 | 3.4 |
| 300 | 3.98 | 153 | 339 | 3.8 |
| 3996 | 4.03 | 140 | 315 | 3.5 |
| B121 | 3.98 | 168 | 363 | 4.2 |
| 3960 | 4.58 | 198 | 386 | 4.6 |
| 3622 | 2.00 | 60 | 170 | 3.0 |
| B118 | 1.82 | 57 | 159 | 3.1 |
| B119 | 1.07 | 27 | 82 | 2.5 |
| 3963 | 3.75 | 127 | 306 | 3.4 |
| 16015 | 0.53 | 8 | —* | 1.5 |
| 3740 | 3.15 | 104 | 267 | 3.3 |
| 3758 | 2.83 | 114 | 248 | 4.0 |
| 3894 | 3.81 | 173 | 381 | 4.6 |
| LSD(0.05) | 0.47 | 16 | 46 | 0.2 |

*Leaves senesced before harvest.

TABLE 4

Symbiotic $N_2$ fixation in peas nodulated by Rhizobium leguminosarum strain 3740 or 3894 and grown in the absence of combined N Original seed N content was subtracted from the mean Kjeldahl N value of at least seven replicate plants on each harvest date.

| Plant age (days) | Rhizobium strain 3740 | 3894 |
|---|---|---|
| | (mg $N_2$ fixed/plant) | |
| 11 | 0 | 0 |
| 17 | 2 | 1 |
| 23 | 12 | 15* |
| 30 | 38 | 66*** |
| 37 | 74 | 118*** |
| 44 | 117 | 202*** |

*, , * - Strain effect significant at p ≦ 0.05, 0.01, or 0.001, respectively.

When plasmid pVW5JI was transferred into strains 300 and 3622, the resulting strains 3996 and B118 maintained the capacity to fix nitrogen, and plant dry weight and N content associated with these strains was not significantly different from the same parameters measured for plants nodulated by the parent strains 300 and 3622 (Table 3). The transfer of pVW5JI and pRL10JI into strain 16015 produced strain 3740 which also was capable of $N_2$ fixation. Transferring to pVW5JI/pRL10JI recombinant plasmid pIJ1019 into strains 300 or 16015 to produce strains B121 or 3758 had little effect on symbiotic properties relative to strains 3996 and 3740, respectively, except for a slight increase in $N_2$ fixation. The same plasmid, pIJ1019, however, had a distinctly deleterious effect on symbiotic performance when it was transferred into strain 3622 (see B119, Table 3). By contrast, plasmid pIJ1008, which carries Hup determinants, produced strains with significantly better symbiotic properties than all other related strains. Strains 3960, 3963 and 3894, all of which express uptake hydrogenase activity in the tritium incorporation assay, produced marked increases in plant dry weight and $N_2$ fixation. The plant dry weight, N content, and leaf area produced by strain 3960 were also significantly greater than Hup+ strain 128C53, from which the Hup determinants in pRL6JI were derived (Table 3). Total plant N concentration (Table 3) was highly correlated with total N content (r=0.932, p≦0.001).

In general, short-term rates of apparent nitrogen fixation calculated from "acetylene reduction" and dihydrogen evolution were consistent with the more definitive measures of $N_2$ fixation based on Kjeldahl N content and $^{15}N$ dilution. Plants nodulated by strain 3894 had $C_2H_2$-reduction rates greater than the rates of plants nodulated by strain 3740 in the same N treatment. The relative efficiency of $N_2$ fixation, defined by Schubert and Evans (1976) as RE=1−($H_2$ evolved/$C_2H_2$ reduced), was greater for Hup+ strain 3894 than for Hup− strain 3740 at all points assayed.

With a few exceptions Rhizobium cells isolated from root nodules and tested in these experiments had characteristics identical to the original inoculant strains.

This research clearly demonstrates the potential for increasing the effectiveness of the Rhizobium-legume symbiosis by selective transfer of plasmids. The presence of plasmid pIJ1008 in strains 3960 and 3963 was associated with 31% and 128% increases in $N_2$ fixation relative to field isolates 300 and 3622 (calculated after subtracting original seed N from values in Table 3). Furthermore, strain 3960 fixed 46% more $N_2$ than field isolate 128C53, the source of pRL6JI from which the Hup+, Nod+, and Fix+ determinants of pIJ1008 are derived. It appears therefore, that the increased effectiveness of the superior strains containing pIJ1008 resulted from their common capacity to recover dihydrogen evolved by nitrogenase. The possibility that the introduction of additional Nod+ and Fix+ determinants ity. It can therefore be used successfully to infect peas.

TABLE 5

Quantitative measurements of pea root nodule activity following inoculation with Hup+ and Hup− strains of R. leguminosarum.

| Inoculant | Characteristic | Acetylene reduction (micromole $C_2H_4$ per plant per h) | Hydrogen evolution (micromole $H_2$ per plant per h) | Tritium incorporation (micromol H—T per g-nodule fresh wt per h) |
|---|---|---|---|---|
| 300 | Field isolate | 5.11 (±0.32) | 3.16 (±0.23) | 0.002 (±0.001) |
| 3740 | 16015 pVW5JI,pRL10JI | 84.6 (±0.24) | 5.01 (±0.30) | 0.001 (±0.001) |
| 128C53 | Field isolate | 7.97 (±0.99) | 0.57 (±0.20) | 0.738 (±0.063) |
| 3892 | 16015 pIJ1007 | 6.84 (±0.48) | 0.32 (±0.04) | 1.013 (±0.112) |
| 3894 | 16015 pIJ1008 | 9.43 (±1.09) | 0.37 (±0.04) | 0.844 (±0.074) | contributed to the improved performance of strains containing pIJ1008 was considered. However the presence of the nodulation plasmid pIJ1019, which also contains additional Nod+ and Fix+ determinants, did not enhance the symbiotic performance of strains B121 or B119 relative to 300 or 3622 respectively. Thus the mere presence of a second nodulation plasmid (pIJ1008) in strains 3960 and 3963 cannot in itself explain their superior symbiotic performance.

EXAMPLE 3

Preparation of strains containing plasmid pIJ1007

This Example can be understood more quickly by referring to the chart of the genealogy of plasmid pIJ1007 which is included as an Appendix to the Examples.

pVW3JI is the plasmid of lower molecular weight present in strain B161 which has been deposited at the National Collection of Industrial Bacteria, previously mentioned, on Oct. 22, 1981 under Accession Number NCIB 11683. Strain B161 contains two plasmids, pRL13JI, present in field isolate strain 128C53, of m.w. 250 Md and pVW3JI of molecular weight 130 Md.

Example 1 was repeated using strain 2515 containing plasmid pVW3JI in place of strain 2517. Gel electrophoresis showed that strain 2515 had an extra band at 130 Md attributable to plasmid pVW3JI which hybridised to Tn5. It lacked pVW5JI, m.w. 165 Md. The frequency of transfer of Kan was $2 \times 10^{-4}$ per recipient. 5 clones tested were found to be Nod+, Fix+, Hup+. When the resultant strain, designated 3856, was used as a donor to 16015, the frequency of transfer of Kan was $5 \times 10^{-7}$ per recipient and out of 15 clones tested 11 were Nod+, Fix+, Hup+. No nodulation occurred when donor strain 2515 was crossed to 16015. The strain 3892 resulting from the cross 3856×16015 gave a plasmid band identical with that of strain 3894 in Example 1. The same experiments were done as listed in Section (f) of Example 1, with the same results. It is concluded that strain 3892 and the Kan transconjugants of subsequent crosses contain a plasmid of m.w. 195 Md which has arisen through recombination of pVW3JI and the non-transmissible plasmid pRL6JI. This plasmid is designated pIJ1007.

pIJ1007 is distinguished from pIJ1008 only by its method of preparation and it is not certain whether or not they are one and the same. These and other experiments indicate that at least they have substantial homogenity of the genome.

Table 5 shows that the strain 3892 (16015 pIJ1007) has the same general beneficial phenotypical behaviour as (16015 pIJ1008), i.e. possesses hydrogen uptake ability. It can therefore be used successfully to infect peas.

EXAMPLE 4

Use of the deposited strains to construct further strains containing pIJ1007 or pIJ1008

The plasmids deposited are in the genetic background of strain B151 (128C53 str 279, lacking the nodulation plasmid pRL6JI). The plasmids, which determine Kanamycin-resistance, are transmissible to other strains of Rhizobium leguminosarum, R trifolii, R phaseoli and R meliloti. Introduction into a field isolate, e.g. strain 3622, could for example be achieved in the following manner, using standard techniques for bacterial crossing.

Stage 1

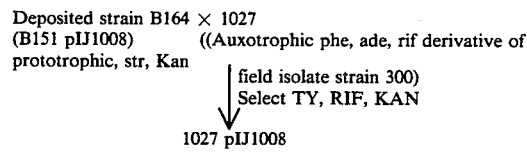

(Auxotrophic strains require supplements e.g. amino acids or nucleoside bases, to the growth medium).

Kan-r derivatives of 1027 would arise at a frequency of c. $10^{-3}$ per recipient as a result of conjugal transfer of pIJ1008. After strain purification this strain would be used as a donor in a subsequent cross to a wild type strain, e.g. 3622. (R. leguminosarum).

Strain 1027 is used here as an example of a strain which allows counter-selection against the donor (B164) because it has rifampicin resistance and can itself be counter-selected against when used as a donor in crosses to field isolate strains, because it is auxotrophic.

Stage 2

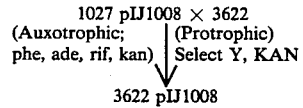

Analogously, deposited strain B163 (i.e. B151 pIJ1007) can be crossed with strain 1027 and the transconjugants selected as above crossed with a wild type strain, for example 3622.

Other auxotrophic strains can be used instead of 1027 in the above procedure. Other wild type (field isolate) strains can be used in place of 3622. Thus pIJ1007 or pIJ1008 can be introduced into a variety of different strains of Rhizobia. When introduced into R. leguminosarum hydrogen uptake ability and a consequential beneficial effect on plant growth can in general be expected.

By a procedure as in stage 1 set out above, the deposited strains B162 and B161 containing plasmids pVW5JI and pVW3JI respectively can be used to generate a culture of strain 1027 containing pVW5JI or pVW3JI and such a strain can be used to repeat the crosses described above in Example 1 and 3 and shown in the genealogical charts. Thus it is possible for recombinant plasmids pIJ1008 and and pIJ1007 or variants thereof to be re-prepared using the deposited strains B162 and B161 respectively and the information given herein. The resultant recombinant plasmids could be variants having the same properties (Nod+, Fix+, Hup+, Kan, Tra+).

APPENDIX

Key to notation and symbols

Plasmids

Natural plasmids of *Rhizobium Leguminosarum* are designated pRL followed by a number and the suffix JI. Synthetic plasmids derived from the natural ones carry the prefix IJ in place of the suffix or carry a prefix VW in place of RL.

Strains

Two genealogical charts are provided showing the origins of the strains used in this specification, all having an ancestry in naturally occurring field isolate strains of *R. Leguminosarum*. The strains have various markers representing, drug resistance or that they will grow only in media supplemented by additional amino acids or nucleotide bases, compared to the natural strain. The symbols used have the following meanings:

ade mutation, requires adenine
kan mutation, resistance to kanamycin sulphate (60 micrograms/ml.)
phe mutation, requires phenylalanine
rif mutation, resistance to rifampicin
spc mutation, resistance to spectinomycin
str mutation, resistance to streptomycin
trp mutation, requires tryptophan The symbol Δ represents deletion of a plasmid or of a genotypic characteristic.

The notation in which a strain number is followed by a plasmid number denotes that the strain retains its plasmids with the addition of the extra plasmid mentioned. For example, 3622 pIJ1008 means that the naturally occurring strain 3622 has acquired the transmissible plasmid pIJ1008 (as a result of a cross from a donor strain containing pIJ1008 or its precursors).

Phenotypic and other symbols

Fix+: Nitrogen fixation as defined by the "acetylene reduction" test (more accurately a test of acetylene-dependent ethylene production) of Beynon et al., Journal of General Microbiology, 120, 421–429 (1980)
Hup+: Hydrogen uptake as defined by uptake of tritium within pea root nodules, according to Bethlenfalvay and Phillips, Plant Physiology, 63, 816–820 (1979)
Kan—r: Denotes that the plasmid is responsible for Kanamycin
or Kan: resistance as defined above.
Med+: Denotes that the plasmid specifies the medium bacteriocin.
Nod+: Formation of root nodules on peas, by method of Beynon et al., supra.
Tn 5: This indicates that the plasmid contains the transposon Tn 5, conferring resistance to kanamycin.
Tra+: Denotes that the plasmid is transmissible by conjugation.

We claim:

1. A recombinant plasmid characterized in that it contains DNA of (1) a first Rhizobium plasmid identifiable as being the same as the plasmid pVW5JI or pVW3JI of lower molecular weight present in the culture of a strain of *Rhizobium leguminosarum* NCIB 11685 or 11683 respectively and (2) a second Rhizobium plasmid found in bacteria of another strain of *Rhizobium leguminosarum*, said second plasmid having Rhizobium genes coding for nodulation, nitrogen fixation and hydrogen uptake ability but which is non-transmissible.

2. A method of preparing a culture of bacteria of the genus Rhizobium, which method is characterized in that
   (1) in a first cross, a donor strain of Rhizobium, containing (a) a Rhizobium plasmid lacking genes coding for nodulation but which is transmissible, is crossed with a recipient strain of Rhizobium, carrying (b) a Rhizobium plasmid having Rhizobium genes coding for nodulation, nitrogen fixation and hydrogen uptake ability but which is non-transmissible, whereby a transconjugant strain carrying a plasmid which is formed from said plasmids (a) and (b) and is a conjugal precursor of a recombinant plasmid (c) having genes coding for nodulation, nitrogen fixation and hydrogen uptake ability and being transmissible is obtained;
   (2) said transconjugant strain is separated from donor and recipient strains and cultured to produce a substantially pure culture thereof;
   (3) in a second cross, the transconjugant strain from the first cross is used as a donor strain and crossed with a plasmid-containing recipient strain whereby a transconjugant strain carrying a recombinant plasmid (c) is obtained; and
   (4) said transconjugant strain from the second cross is separated from donor and recipient strains and cultured to produce a substantially pure culture thereof.

3. A method according to claim 2 characterized in that the transmissible plasmid (a) carries at least one drug-resistance gene.

4. A method according to claim 3 characterized in that the transmissible plasmid is pVW5JI or pVW3JI, identifiable as being the same as the plasmid of lower molecular weight present in the culture of a strain of *Rhizobium leguminosarum* NCIB 11685 (pVW5JI) or NCIB 11683 (pVW3JI), and a kanamycin-resistant transconjugant strain is separated in each cross.

5. A method according to claim 2 characterized in that the transmissible plasmid (a) contains a selectable determinant.

6. A method according to claim 2, characterized in that the donor and recipient strain are of the species *Rhizobium leguminosarum*.

7. A method of imparting hydrogen uptake ability to bacteria of the genus Rhizobium, which method is characterized in that (1) a strain of *Rhizobium leguminosarum* NCIB 11684 or NCIB 11682, as a donor strain, is crossed with a recipient strain of *Rhizobium leguminosarum* to produce a kanamycin-resistant transconjugant strain, said recipient strain being one which permits selection of the transconjugant strain against the donor and recipient strains and which allows the transconjugant strain to be selected against when used as a donor in a subsequent cross with another strain of *Rhizobium leguminosarum*, (2) said transconjugant strain is separated from the donor and recipient strains and cultured to produce a substantially pure culture thereof; (3) in a second cross the transconjugant strain obtained from the first cross is used as a donor strain and crossed with a recipient strain of *Rhizobium leguminosarum* to produce a kanamycin-resistant transconjugant strain and (4) said transconjugant strain from the second cross is separated from the donor and recipient strains to produce a biologically pure culture thereof.

8. A method according to claim 7 characterized in that the recipient strain for the first cross is auxotrophic and has resistance to a drug other than kanamycin.

9. A method according to claim 7 or 8 wherein the recipient strain for the second cross is a naturally occurring strain.

10. A Rhizobium plasmid pIJ1008 having Rhizobium genes coding for streptomycin and kanamycin resistance, nodulation, nitrogen fixation and hydrogen uptake properties, which is transmissible and which is the plasmid of lowest molecular weight present in the culture of a strain of *Rhizobium leguminosarum* NCIB 11684 by virtue of the fact that it migrates the fastest on agarose gel in a gel electrophoresis determination in which a gel of 0.7% agarose in Tris-borate buffer of pH 8.3 is subjected to electrophoresis at 25 mA and 100 volts at 4° C. for 16 to 20 hours in the dark.

11. A Rhizobium plasmid pIJ1007 having Rhizobium genes coding for streptomycin and kanamycin resistance, nodulation, nitrogen fixation and hydrogen uptake properties, which is transmissible and which is the plasmid of lowest molecular weight present in the culture of a strain of *Rhizobium leguminosarum* NCIB 11682 by virtue of the fact that it migrates the fastest on agarose gel in a gel electrophoresis determination in which a gel of 0.7% agarose in Tris-borate buffer of pH 8.3 is subjected to electrophoresis at 25 mA and 100 volts at 4° C. for 16 to 20 hours in the dark.

12. A biologically pure culture of bacteria of the genus Rhizobium characterized in that it contains a plasmid selected from the group consisting of pIJ1008 and pIJ1007.

13. A culture according to claim 12 of bacteria of the species *Rhizobium leguminosarum*.

14. A biologically pure culture of bacteria of the genus Rhizobium containing a recombinant plasmid characterized in that said plasmid contains DNA of (1) a first Rhizobium plasmid identifiable as being the same as tha plasmid pVW5JI or pVW3JI of lower molecular weight present in the culture of a strain of *Rhizobium leguminosarum* NCIB 11685 or 11683 respectively and (2) a second Rhizobium plasmid found in bacteria of another strain of *Rhizobium leguminosarum*, said second plasmid having Rhizobium genes coding for nodulation, nitrogen fixation and hydrogen uptake ability but which is non-transmissible.

* * * * *